United States Patent [19]

Kennett et al.

[11] Patent Number: 4,652,522

[45] Date of Patent: Mar. 24, 1987

[54] CONTINUOUS LYMPHOCYTE CELL LINES, THEIR PRODUCTION AND USE

[75] Inventors: Roger H. Kennett, Drexel Hill; Zdenka L. Jonak, Philadelphia, both of Pa.

[73] Assignee: The University of Pennsylvania, Philadelphia, Pa.

[21] Appl. No.: 510,825

[22] Filed: Jul. 5, 1983

[51] Int. Cl.$^4$ .................. C12P 21/00; C12N 5/00; C12N 15/00; C12R 1/91

[52] U.S. Cl. .................. 435/68; 435/240; 435/172.1; 435/948; 935/52

[58] Field of Search .......... 435/240, 172.3, 948, 435/68, 172.1; 935/93, 100, 104, 52

[56] References Cited

U.S. PATENT DOCUMENTS

| | | | |
|---|---|---|---|
| 4,001,080 | 1/1977 | Goust et al. | 435/91 |
| 4,108,983 | 8/1978 | Wallack | 424/89 |
| 4,172,124 | 10/1979 | Koprowski et al. | 424/85 |
| 4,195,074 | 3/1980 | Safford, Jr. | 424/12 |
| 4,196,265 | 4/1980 | Koprowski et al. | 435/2 |
| 4,271,145 | 6/1981 | Wands et al. | 424/85 |
| 4,332,893 | 6/1982 | Rosenberg | 435/68 |
| 4,334,016 | 6/1982 | Furukawa | 435/5 |
| 4,464,465 | 8/1984 | Lostrom | 435/68 |
| 4,529,694 | 7/1985 | Lazarus et al. | 435/68 |
| 4,565,687 | 1/1986 | Khazaeli et al. | 424/1.1 |

FOREIGN PATENT DOCUMENTS 0057107  8/1982  European Pat. Off. .......... 435/948

OTHER PUBLICATIONS

Crowe et al., Experiments with Normal and Transformed Cells, Cold Spring Harbor, N.Y., 1978, pp. 28, 58–59.
Weinberg, (1981) Biochimica et Biophysica Acta 651: 25–35.
Krontiris et al., (1981) Proceedings of the National Academy of Sciences USA 78: 1181–1184.
Shih et al., (1981) Nature (London) 290: 261–264.
Perucho et al., (1981), Cell 27: 467–476.
Littlefield (1982) Science 218: 215–216.
Smith et al., (1982) Proceedings of the National Academy of Sciences USA 79: 1964–1968.
Pellicer et al., (1980) Science 209: 1414–1422.
Cline et al., (1980) Nature (London) 284: 422–425.
Mercola et al., (1980) Science 208: 1033–1035.
Anderson et al., (1980) Proceedings of the National Academy of Sciences USA 77: 5399–5403.
Anderson et al., (1981) Scientific American 245: 106–121.
Jonak and Kennett, "Transfection of Primary Mouse Lymphocytes with Human Tumor DNA: Production of Continuous Cell Lines Producing Monoclonal Antibodies", Second Annual Congress for Hybridoma Research, Abstract, (Feb. 6–10, 1983).
Jonak and Kennett, (1983) Hybridoma 2: 124 (reprint of above abstract).
Biotechnology Newswatch, Feb. 21, 1983, pp. 1–2.
Immunology Today, Mar. 1983, p. 2.
Genetic Engineering News, May/Jun. 1983, p. 7.
Science News, Feb. 19, 1983, p. 125.

Primary Examiner—Thomas G. Wiseman
Assistant Examiner—Karen Maurey
Attorney, Agent, or Firm—Banner, Birch, McKie & Beckett

[57] ABSTRACT

A method for producing continuous B lymphocyte cell lines and monoclonal antibodies by such lines is provided. DNA isolated from neoplastic cells is introduced into stimulated lymphocytes. Individual cells that have been transformed by the added DNA and that produce antibodies are clonally expanded. Cultures of these continuous cells are employed to produce monoclonal antibodies.

22 Claims, No Drawings

CONTINUOUS LYMPHOCYTE CELL LINES, THEIR PRODUCTION AND USE

TECHNICAL FIELD

The present invention is directed to the production of continuous B lymphocyte cell lines by transfection with oncogenic DNA.

BACKGROUND OF THE INVENTION

Primary lymphocytes, both human and animal, are difficult to maintain in continuous culture. Short term cultures of B-lymphocytes can be maintained long enough to produce limited amounts of specific antibody. Generally, it is necessary to repeatedly stimulate primary, antigen-specific lymphocytes with antigen in media containing expensive lymphokines. Failure to include such lymphokines, either exogenously or by autologous monocytes, often results in cell death. Attempts to produce continuous mouse lymphocyte cell lines by infection of stimulated cells with viruses such as Abelson virus produce only cell lines with pre-B-cell characteristics. Infection of human B-lymphocytes with Epstein Barr virus has had limited success. Such cell lines, however, usually make limited amounts of antibody for a period of only a few weeks.

The advent of hybridoma technology provided a method of producing lymphocyte cell lines that are continuous (i.e., maintainable in culture indefinitely without added lymphokines) and stable (i.e., maintaining antigen-specific immunological function such as antibody production). Basically, the procedure involves the fusion of two somatic cell; a cancerous B lymphocyte (myeloma) and a normal, stimulated B lymphocyte that produces the desired antibody. Although hybridoma technology has revolutionized immunology, the procedure is limited by the availability of plasmacytoma cell lines suitable for hybridoma production. In addition, fusion efficiency (i.e., the relative number of hybridomas with a desired function recovered from the fusion media) is low, particularly for fusions between human lymphocytes.

Certain cell lines have been susceptible to transformation with exogenous DNA. Mouse fibroblast cells have previously been transformed by transfection with oncogenic DNA. See Weinberg, (1981) *Biochem. Biophys. Acta* 651: 24–35; Krontiris et al., (1981) *Proc. Natl. Acad. Sci. USA* 78: 1181–1184; Shih et al., (1981) *Nature* (London) 290: 261–164; Perucho et al., (1981) *Cell* 27: 467–476. Hamster fibroblast cells have also been transformed by transfection with oncogenes. See Smith et al., (1982) *Proc. Natl. Acad. Sci. USA* 79: 1964–1968. Other cells, such as mouse bone marrow cells and fibroblast cells have been transfected by non-oncogenic DNA, such as the thymidine kinase gene from the herpes simplex virus. See Cline et al., (1980) *Nature* (London) 284: 422–425; Mercola et al., (1980) *Science* 208: 1033–1035; Pellicer et al., (1980) *Science* 209: 1414–1422. Very few cell types, however, have been identified that are susceptible to transfection with exogenous DNA.

SUMMARY OF THE INVENTION

An object of the present invention is to provide continuous lymphocyte cell lines and a method for the production of such cell lines.

It is also an object of the present invention to provide continuous cell lines of human lymphocytes.

Another object of the present invention is to provide continuous cell lines of antibody-producing lymphocytes.

A further object of the present invention is to provide a method of transforming lymphocytes with exogenous, oncogenic DNA.

These and other objects of the present invention are achieved by one or more of the embodiments below.

In one embodiment, the present invention provides a method of producing a continuous lymphocyte cell line comprising: (a) providing normal, stimulated B lymphocytes; (b) transfecting said lymphocytes with exogenous DNA isolated from a neoplastic cell; (c) recovering from said transfected lymphocytes a transformed lymphocyte; and (d) clonally expanding said transformed lymphocyte to a cell line that stably maintains the production of monoclonal antibodies.

In another embodiment, the present invention also provides biologically pure cultures of the continuous, monoclonal antibody-producing cell lines produced by the above method.

Still another embodiment of the present invention provides a method of producing monoclonal antibodies comprising growing the above cell line and recovering the antibodies produced by said cell line.

The present invention provides a continuous lymphocyte cell line that maintains production of monoclonal antibodies as well as a method of producing such a continuous lymphocyte cell line. The method of the present invention does not require the fusion of a plasmacytoma cell and a normal lymphocyte. Only the particular stimulated, primary B lymphocyte cell need be provided to produce the continuous cell lines of the present invention. It is not necessary, therefore, to obtain a selectable (e.g., HAT sensitive) mutant of a cancerous lymphocyte as required in the production of hybridomas. Furthermore, transformation efficiency is improved in the method of the present invention relative to hybridoma techniques. The cell lines of the present invention are stable and are particularly useful for the production of monoclonal antibodies.

DESCRIPTION OF THE PREFERRED EMBODIMENT

Generally, the continuous cell lines of the present invention are made by transfecting stimulated, normal primary B lymphocytes with exogenous DNA isolated from a neoplastic cell. Individual cells that have been transformed and produce monoclonal antibodies are clonally expanded and cultures of these continuous cells are employed to produce monoclonal antibodies.

The continuous lymphocyte cell lines of the present invention differ from hybridoma cell lines in several respects. For example, the cell lines of the present invention are not somatic cell hybrids, as are hybridomas. The claimed cell lines are produced by the incorporation of oncogenic DNA into a normal lymphocyte genome (i.e., transfection), not the "mixing" of the genomes of a normal and malignant lymphocyte (i.e., fusion). The DNA isolated from a neoplastic cell that transfects the normal lymphocytes is also employed in an extracellular form, in contrast to the whole myeloma cells employed to make hybridomas. Other differences are readily apparent to those of skill in the art.

The stimulated, normal, primary B lymphocytes employed in the present invention can be either human or animal, preferably mammalian. Suitable animal lymphocytes include, but are not limited to, lymphocytes of mice, rats, guinea pigs, rabbits, dogs, sheep, cats, cattle and horses. A "normal" lymphocyte is a noncancerous lymphocyte. A "stimulated" B lymphocyte is a B lymphocyte that has been challenged by the antigen of interest and has differentiated into an antibody-producing cell, the antibodies being specific for the chosen antigen. Each B lymphocyte produces antibody of only one idiotype; both light chain sequences and heavy chain sequences with a variable region providing specificity for one antigenic determinant.

Monoclonal antibodies can be employed for therapeutic purposes, as is well known in the art. While it is possible to employ monoclonal antibodies of one species in another, it is preferred to select the lymphocyte source from the same species as the recipient of the antibodies. In other words, if the antibodies are intended for use in a human patient, human B lymphocytes should be employed in the present invention. If nontherapeutic uses are intended (e.g., immunoassays), generally any type of antibody, such as mouse, may be readily employed.

In the method of the present invention, it is acceptable to employ a preparation of mixed lymphocytes that contains normal, stimulated B lymphocytes as the recipients of the transfecting DNA. Of course, populations of just B lymphocytes can also be employed, but it is unnecessary to isolate them. Mixed lymphocyte populations containing stimulated, normal B lymphocytes are, therefore, preferred since mixed populations are comparatively easier to obtain. Heterogeneous animal lymphocyte populations, such as mouse lymphocytes, that contain stimulated, normal B lymphocytes can be readily obtained from the spleen by methods known in the art. See, e.g., *Monoclonal Antibodies*, p. 366 (R. H. Kennett, T. J. McKearn and K. B. Bechtol eds. 1980). Mixed human lymphocyte populations containing normal, stimulated B lymphocytes can be isolated, for example, from the peripheral blood by methods known in the art. See, e.g., Boyum, (1978) *Scand. J. Lab. Clin. Invst.* 21: 77.

The normal, stimulated B lymphocytes are artificially transfected by exogenous DNA isolated from neoplastic cells resulting in the transformation of certain cells. Transfection is the uptake and incorporation into the genome of the exogenous DNA. Transformation refers to the changing of a normal cell into a malignant and, therefore, continuous cell as a result of transfection. A continuous cell line is one that can proliferate for an unlimited number of generations in culture.

Exogenous DNA is DNA isolated from a source other than the transfected lymphocyte. The exogenous DNA employed in the present invention to transfect normal, stimulated B lymphocytes is obtained from neoplastic cells. It is not necessary that the neoplastic cell and transfected cell be of the same species. DNA from diverse neoplastic cells, such as cancerous human bladder cells and mouse fibroblast cells, have demonstrated the ability to transform cell lines. The ability of DNA from any particular neoplastic cell to transform lymphocytes can be readily estabished by one of skill in the art through screening. See, e.g., Krontiris et al., (1981) *Proc. Natl. Acad. Sci. USA* 78: 1181-1184; Perucho et al., (1981) *Cell* 27: 467-476; Shih et al., (1981) *Nature* (London) 290: 261-264.

A preferred source of DNA for the transformation of lymphocytes is DNA from malignant lymphocytes, such as B lymphocytes. A particularly preferred source is a malignant pre-B cell such as the human acute lymphocytic leukemia cell line Reh, which has been well characterized and described in the literature. See, e.g., Goutner et al., (1977) *Nature* (London) 267: 841-843; Venuat et al., (1981) *Cytogenet. and Cell Genet.*, 3: 327-334. These cells can be maintained in RPMI 1640 media with 10% fetal bovine serum (FBS). Another B cell source of transfecting DNA is a malignant plasma cell such as the mouse plasmacytoma cell line SP2/0-Ag14. Both the Reh and the SP2/0-Ag14 cell lines were deposited with the American Type Culture Collection (ATCC), 12301 Parklawn Drive, Rockville, Md. 20852, on Mar. 30, 1983 under accession numbers CRL 8286 and CRL 8287, respectively.

It is not necessary to isolate the transfecting oncogene(s) from the neoplastic cells employed in the present invention. All of the DNA isolated from the neoplastic cells can be used to transfect the recipient lymphocytes. Techniques for isolating DNA from cells are well known in the art. Most of this DNA, however, does not participate in the transformation of primary transfectants and, therefore, is unnecessary. If desired, the DNA portions containing the operative oncogene(s) can be identified by transfecting additional lymphocytes with DNA from the primary transfectants. These secondary transfectants will lose large amounts of the nonessential DNA found in primary transfectants, thus identifying the DNA containing essential oncogenic regions.

Various methods of transfecting cells with exogenous DNA are known in the art. Those methods include, but are not limited to, treatment of the cells with a calcium phosphate DNA coprecipitate, DEAE-dextran, microinjection, etc. See, e.g., Anderson et al., (1980) *Proc. Natl. Acad. Sci. USA* 77: 5399-5403; Weinberg (1981) *Biochem. Biophys. Acta* 651: 25-23; Graham et al., (1973) *Virology* 52: 456-467. The preferred method of transfection is treatment of the lymphocytes with a calcium phosphate DNA coprecipitate in conjunction with a polyethylene glycol (PEG) and dimethylsulfoxide (DMSO) "shock" treatment of the recipient lymphocytes. Generally, this involves suspending and centrifuging the recipient cells in serum-free medium containing about 35% PEG 1000 and about 5% DMSO. Variations of the above technique (including, inter alia, variations in concentrations, PEG molecular weight, including protein in the incubation mixture) are within the skill of the art.

After transfection, transformed cells are identified by sustained growth in culture media. Recovered transformed cells are then tested for production of antibodies by standard methods known in the art. Cells showing positive antibody production can be clonally expanded into continuous antibody-producing cell lines and maintained in biologically pure cultures (i.e., substantially free of other cell types). These clonally derived cell lines can be stably maintained in culture. The cell lines of the present invention can also be grown in culture and monoclonal antibodies recovered by techniques well known in the art for hybridoma cell lines (e.g., precipitation from supernatants). See generally, *Monoclonal Antibodies*, pp. 372-375, 403-406 (R. H. Kennett, T. J. McKearn and K. B. Bechtol eds. 1980) [hereinafter cited as *Monoclonal Antibodies*].

An illustrative protocol for production of continuous antibody-producing cell lines is given below. The details of this protocol are only suggested and variations in the specific techniques are readily within the skill of the art.

Stimulated primary human lymphocytes directed against an antigen, such as tetanus toxoid, for example, can be readily collected. A volunteer is given a standard booster dose of tetanus toxoid. Samples of peripheral blood (e.g., 10 ml) are then obtained by venipuncture on days 0, 3, 6, 9 and 12 post-immunization. Ficoli-Paque treatment, for example, can be used to isolate lymphocytes from the majority of erythrocytes in a blood sample. Lymphocytes are then pelleted and rinsed twice with cell culture medium containing serum and once with serum-free medium. The washed lymphocytes can then be used as recipients for transfecting DNA.

Stimulated primary human lymphocytes can also be obtained by in vitro immunization with a desired antigen. First, lymphocytes from the peripheral blood are isolated as described above. These cells are then placed into serum-free medium. The serum-free medium can be prepared, for example, by adding to 500 ml of RPMI 1640 the following: 0.5 ml ITS (2.5 mg insulin, 2.5 mg transferrin, 2.5 ug selenium), 1 ul beta-mercaptoethanol, 1 ul ethanolamine, 150 mg glutamine, 10 ug/ml gentamicin and 5 ml stock glucose solution (25 g/100 ml). The desired antigen is then added to the cells in serum-free medium. The antigen can be either whole, irradiated cells or a soluble antigen. The cells are incubated with the antigen for about 5 to 7 days and washed by centrifugation in serum-free HY medium. The lymphocytes are then suitable for transfection with oncogenic DNA.

The stimulated human lymphocytes are transfected with oncogenic DNA, such as total DNA isolated from the acute lymphocytic leukemia cell line Reh or the plasmacytoma cell line SP2/0-Ag 14. The DNA is isolated and, according to the preferred embodiment, prepared for transfection by calcium-phosphate coprecipitation by methods well-known in the art. See, e.g., Graham, et al., (1973) *Virology* 52: 456–467. Stimulated lymphocytes are suspended with the coprecipitated DNA and then preferably treated with PEG by resuspending and centrifuging the cells in medium with, for example, 37% PEG 1000 and 5% DMSO. The exact amount of PEG and DMSO can be readily varied, if desired, by one of skill in the art. The cells can then be resuspended in fresh medium and centrifuged again before distributing them, for example, in the wells of microplates. Transformed cells appear in about two to three weeks as clumps of cells sightly larger in size than non-transformed cells.

The following examples are included for illustrative purposes only and are not intended to limit the scope of this invention.

EXAMPLE I

Preparation of Oncogenic DNA for Transfection

The acute lymphocytic leukemia cell line Reh was grown in RPMI 1640 media with 10% FBS. Cells were harvested and washed three times in Dulbecco's Ca and Mg free phosphate buffered saline (PBS).

The cells were suspended in 1 ml of 0.1M Tris, pH 7.0, 0.1M NaCl, 0.05M EDTA, 1% NP40, and vortexed gently. Lysis solution (0.1M Tris, pH 7.9, 0.1M NaCl, 0.05M EDTA and 0.5% SDS) was then added, to which proteinase K (final concentration 50 ug/ml) was added just prior to use. After incubation at 37 C. for two hours, the preparation was extracted with one-half volume of redistilled phenol plus one-half volume of chloroform-isoamyl alcohol (24:1). The aqueous phase was reextracted with an equal volume of chloroform-isoamyl alcohol. After addition of 0.1 volume of 3M sodium acetate, pH 5, and 2.5 volumes of cold 95–100% alcohol, the precipitated DNA was gently spooled on a sterile glass rod. The DNA was dissolved in a small volume of 0.05M Tris, pH 7.9, 0.05M NaCl, 0.01M EDTA (TEN), dialyzed against the same buffer, and the A260 and A280 were measured. Prior to use in transfection, the DNA was sterilized by ethanol precipitation and resuspended in sterile TEN. The DNA employed in transfections was coprecipitated according to the method of Graham, et al., (1973) *Virology* 52: 456–467. To 20 ug of DNA was added 75 ul of solution A (19 ml sterile $H_2O$, 5 ml 10x salt solution/1.37M NaCl, 0.05M KCl, 0.007M $Na_2HPO_4.7H_2O$/, 0.06M dextrose, 1 ml Hepes buffer, pH 7.0) and mixed gently. Then, 75 ul of solution B (1 ml 2M $CaCl_2$, 3 ml $H_2O$) was added dropwise while air bubbled through the DNA solution. This mixture was vortexed for 5 seconds at maximal agitation. Precipitate was then allowed to form for 45–60 minutes at room temperature.

EXAMPLE II

Production of Antibody-Producing Continuous Mouse Lymphocyte Cell Line

A. Stimulation of Lymphocytes

Mouse lymphocytes were stimulated in vivo with a subcutaneous injection of $10^6$ Reh cells three weeks prior to the transfection. The period between stimulation and transfection may be varied. The primed lymphocytes were removed from the spleen and treated as reported for hybridoma production in Kennett et al., (1978) *Current Topics in Microbiol, and Immunol.* 81: 77–94.

B. Transfection of Lymphocytes

Stimulated mouse lymphocytes were washed by centrifugation and suspended in HY medium without serum (2 ml per $5 \times 10^7$ cells). Thirty micrograms of coprecipitated DNA from Example I was added and the mixture was incubated at 37 C. for 2 hours. The cells were gently resuspended in PEG mixture (35% PEG 1000 and 5% DMSO in HY medium without serum) and centrifuged at 1000 rpm for 5 minutes.

After resuspending cells in 5 ml of HY medium without serum, another 5 ml of the same medium with 10% FBS was added and the suspension was centrifuged for 10 minutes at 1000 rpm. Cells were suspended in 15 ml of TY medium and distributed dropwise into three 96-well microplates. Medium was added once a week.

After approximately 14–20 days, the transformed lymphocytes appeared as clumps of cells slightly larger in size compared to non-transformed lymphocytes. These cells were passaged to additional wells in the same size plates and then to wells of 24-well plates before being passaged to flasks.

The cells were cloned in TY medium (semi-solid agarose) as described previously for hybridomas. Kennett et al., (1978) *Current Topics in Microbiol, and Immunol.* 81: 77–97. TY medium is prepared by making the following additions to 500 ml of HY medium: 1 ml ITS (Collaborative Research, 5 mg insulin, 5 mg transferrin, and 5 ug selenium), 2 ul beta-mercaptoethanol, 2 ul ethanolamine and 20% FBS. See *Monoclonal Antibodies,* supra, pp. 365–367.

In early experiments, equal volumes of this supplemented medium and HY medium with 10% FBS conditioned by mid-log ($6 \times 10^5$/ml) growth of the plasmacytoma line Sp2/0-Ag14 were added together and filtered through a 0.2 u filter. See *Monoclonal Antibodies*, supra, pp. 372-373. An alternative T-RPMI medium was used for growth of some transfectants. T-RPMI medium is prepared by making the following additions to 500 ml of RPMI 1640: 1 ml ITS (5 mg insulin, 5 mg transferrin, 5 ug selenium), 2 ul beta-mercaptoethanol, 2 ul ethanolamine, 150 mg glutamine, gentamicin (10 ug/ml) and 20% (v/v) FBS. It has been found that an even more effective supplement to TY or T-RPMI medium is medium conditioned by incubation with mouse spleen cells at a concentration of $10^4$/ml for 8-10 days.

C. Antibody Production by Transformed Lymphocytes

Transformed lymphocytes were tested for antibody production. Antibody production was determined by testing transfectant supernatants with an enzyme-linked antibody assay described in *Monoclonal Antibodies*, supra, pp. 376-377. SDS-PAGE analysis of the secreted immunoglobulin chains was done as reported previously. Id., pp. 407-411. Prior to electrophoresis, the immunoglobulin chains were precipitated by binding to sepharose-protein A coated with rabbit anti-mouse immunoglobulin or rabbit anti-human immunoglobulin. The pellet was boiled in SDS sample buffer and the sample applied to SDS-PAGE.

Table I shows the results of two separate lymphocyte transfections. In each lymphocyte transfection, more than 100 of the 288 wells plated showed clumps of dividing lymphocytes. In a control transfection done with human placental DNA, only four wells showed any sign of lymphocyte growth, and attempts to passage these cells were unsuccessful. On the other hand, cells growing in the wells transfected with Reh DNA could be passaged and cloned in semi-solid agarose.

From these initial experiments, nine lymphocyte transfectants were chosen on the basis of their growth rates and concentrated on for further analysis. These have been in culture for more than nine months and can be cloned in agarose. At early stages of their growth in culture, these cells contain only acrocentric chromosomes and have a modal number of 40.

Initial screening indicated that seven of the nine transfectants selected above had detectable antibody in the primary wells in which they were detected. After being passaged for nine months, three out of four transfectants from the first experiment still produce specific antibodies in the culture supernatant. Analysis of the supernatants of four of these transfectants by radial immunodiffusion detected secretion of mouse immunoglobulin chains by three of these cell lines.

TABLE I

| DNA | Total Transformants/ Total Wells | Continuous Lines/Total Transformants* | Transformants per ug DNA/$10^6$ cells | Lines Making Secific Ab./ Tested Lines |
|---|---|---|---|---|
| Placental | 4/288 | 0/4 | — | 0/4 |
| Reh 1 | 105/288 | 35/105 | 0.07 | 3/4 (3/4)** |
| Reh 2 | 157/288 | 47/157 | 0.1 | 11/35 (2/5)** |

*These were chosen because they grew well under the conditions in culture at the time. It is not clear how many would have been continous now that initial culture conditions have been optimized.
**Numbers in parenthesis are stable lines producing specific antibody/stable lines derived from transfection.

D. Detection of Human DNA in Transfected Lymphocytes

The human Alu sequence cloned in plasmid pBR322 was transformed into *E. coli* DH1 and purified using the procedures described in Holmes et al., (1981) *Anal. Biochem.* 114: 193-198. The purified probe, designated BLUR8 and labeled using the procedure described in a nick translation kit (BRL). One microgram of probe was labeled with all four bases (50 uCi each). The specific activity of the labeled probe was between $10^7$ and $10^8$ cpm/ug DNA.

Purified DNA (15 ug) was precipitated with ethanol, resuspended in 32 ul of water, 4 ul of 10 X reaction buffer and 4 ul of restriction enzyme was added (40 units). The samples were incubated overnight at 37 C. and 0.1 volume of tracking dye solution was added before loading the samples on the agarose gel. Agarose (Gibco) was prepared (0.8%) and boiled for 2 minutes, cooled to 50 C. and poured to a thickness of 4 mm. The gel buffer was Tris-borate pH 8.3. Prior to loading on the gel, the samples were incubated at 65 C. for five minutes. The gel was run on a horizontal apparatus (BRL, model H4) for 4 hours at 90 mA. The DNA was stained with ethidium bromide and observed under UV light to confirm the restriction of the DNA.

Fragmented DNA was prepared by soaking the gel in 0.25N HCl for 10 minutes, denatured by soaking with 1.5M NaCl and 0.5N NaOH, and neutralized by soaking in 3M NaCl, 0.5M Tris-HCl, pH 7.4. Denaturation and neutralization were done twice with a 30 minute incubation for each. Blotting was done using 3MM paper, paper towels, the gel, and nitrocellulose paper (Schieicher and Schuell, Keene, N.H.). The buffer was 20 X SSC. The transfer was done overnight at room temperature. The nitrocellulose paper was then baked in a vacuum oven at 80 C. for 3-4 hours and then placed in a resealable plastic bag.

A prehybridization mixture (Denhardt's solution, 0.1% SDS, 25 ug/ml salmon sperm DNA, 5 X SSC) was added and the membrane incubated overnight at 65 C. The prehybridization mixture was replaced with hybridization mixture (prehybridization mixture plus 5% dextran sulfate) with the labeled probe. After overnight incubation at 65 C., the paper was washed with 0.5% SDS, 2 X SSC at 65 C. The blot was wrapped in plastic wrap and exposed to X-ray film with an intensifying screen for 2-7 days.

Three primary lymphocyte transfectants were analyzed. Each showed the presence of a large number of ALU sequences indicating that human DNA from the Reh cell line was incorporated by these cells.

EXAMPLE III

Production of Antibody-Producing Continuous Human Lymphocyte Cell Line

Human lymphocytes were transfected employing a modification of the procedures described in Examples I and II.

Human lymphocytes were isolated from peripheral blood by Ficoli-Paque treatments. The Ficoli-Paque was carefully layered under the suspension of cells in a conical tube. The sample was centrifuged at 2,000 rpm for 20 minutes at room temperature. Cells were then harvested from the interface plus most of the Ficoli-Paque layer and washed three times with medium.

Human lymphocytes were then washed with serum-free medium and counted. The cells were resuspended in serum-free medium at a concentration $10^6$ human lymphocytes/ml of medium. Serum-free medium was prepared by adding to 500 ml of RPMI 1640: 0.5 ml ITS (2.5 mg insulin, 2.5 mg transferrin, 2.5 ug selenium), 1 ul of B-mercaptoethanol, 1 ul ethanolamine, 150 mg glutamine, 10 ug/ml gentamicin plus 5 ml of stock glucose solution (25 g/100 ml).

The human lymphocytes were then immunized in vitro with Reh cells as the antigen. The Reh cells were first irradiated (4500R) and then washed with serum-free medium. The Reh cells were then suspended with human lymphocytes ($10^5$ Reh cells/$10^6$ lymphocytes) at a total cell concentration of about $10^6$ cells/ml and incubated for five days at 37 C. in an atmosphere of 5% $CO_2$ and 95% air.

The cells were then washed with serum-free HY medium and then transfected in TY medium with 94 ug of Reh-DNA/$3 \times 10^6$ lymphocytes according to the method of Example II. In some experiments, irradiated rabbit fibroblasts (4500 R) were used as a feeder layer.

The above examples describe certain embodiments of the present invention. Variations will readily occur to those of skill in the art. The present invention, therefore, is limited only by the appended claims.

We claim:

1. A method of producing a continuous lymphocyte cell line comprising:
   (a) providing normal, stimulated B lymphocytes;
   (b) transfecting said lymphocytes with exogenous DNA isolated from a neoplastic cell, said DNA having the ability to transform lymphocytes;
   (c) recovering from said transfected lymphocytes a transformed lymphocyte; and
   (d) clonally expanding said transformed lymphocyte to a continuous cell line that stably maintains the production of monoclonal antibodies.

2. The method of claim 1 wherein said normal, stimulated B lymphocytes are human lymphocytes.

3. The method of claim 1 wherein said normal, stimulated lymphocytes are mouse lymphocytes.

4. The method of claim 1 wherein said neoplastic cell is a malignant lymphocyte.

5. The method of claim 2 wherein said neoplastic cell is a malignant lymphocyte.

6. The method of claim 3 wherein said neoplastic cell is a malignant lymphocyte.

7. The method of claim 1 wherein said neoplastic cell is a malignant B lymphocyte.

8. The method of claim 2 wherein said neoplastic cell is a malignant B lymphocyte.

9. The method of claim 3 wherein said neoplastic cell is a malignant B lymphocyte.

10. The method of claim 1 wherein said neoplastic cell is a Reh leukemia cell.

11. The method of claim 2 wherein said neoplastic cell is a Reh leukemia cell.

12. The method of claim 3 wherein said neoplastic cell is a Reh leukemia cell.

13. The method of claim 1 wherein said transfection comprises treatment of said normal, stimulated B lymphocytes with a calcium phosphate DNA coprecipitate in conjunction with treatment of said lymphocytes with polyethylene glycol and dimethylsulfoxide.

14. The method of claim 2 wherein said transfection comprises treatment of said normal, stimulated B lymphocytes with a calcium phosphate DNA coprecipitate in conjunction with treatment of said lymphocytes with polyethylene glycol and dimethylsulfoxide.

15. The method of claim 3 wherein said transfection comprises treatment of said normal, stimulated B lymphocytes with a calcium phosphate DNA coprecipitate in conjunction with treatment of said lymphocytes with polyethylene glycol and dimethylsulfoxide.

16. A continuous, stable, antibody-producing cell line produced by the method of claim 1.

17. A continuous, stable, antibody-producing cell line produced by the method of claim 2.

18. A continuous, stable, antibody-producing cell line produced by the method of claim 3.

19. A biologically pure culture of the continuous, stable, antibody-producing cell line produced by the method of claim 1.

20. A method of producing monoclonal antibodies comprising growing the cell line of claim 16 and recovering the antibodies produced by said cell line.

21. A method of producing monoclonal antibodies comprising growing the cell line of claim 17 and recovering the antibodies produced by said cell line.

22. A method of producing monoclonal antibodies comprising growing the cell line of claim 18 and recovering the antibodies produced by said cell line.

* * * * *